United States Patent [19]

Ronco et al.

[11] Patent Number: 4,650,867

[45] Date of Patent: Mar. 17, 1987

[54] PROCESS FOR THE PREPARATION OF 2,4,6-TRIS(AMINOPHENYLAMINO)TRIAZINES

[75] Inventors: Ronald Ronco, Pfeffingen; Willy Stingelin, Reinach; Ernst Hänggi, Riehen, all of Switzerland

[73] Assignee: Ciba-Geigy Corporation, Ardsley, N.Y.

[21] Appl. No.: 841,494

[22] Filed: Mar. 19, 1986

[30] Foreign Application Priority Data

Mar. 26, 1985 [CH] Switzerland ............... 1315/85

[51] Int. Cl.[4] .................................... C07D 251/70
[52] U.S. Cl. ............................................ 544/197
[58] Field of Search ................................. 544/197

[56] References Cited

FOREIGN PATENT DOCUMENTS 1279351  6/1972  United Kingdom .

Primary Examiner—John M. Ford
Attorney, Agent, or Firm—Edward McC. Roberts; Kevin T. Mansfield

[57] ABSTRACT

A process for the preparation of 2,4,6-tris(aminophenylamino)triazines by condensing s-trichlorotriazine with 3 equivalents of a partially protected phenylenediamine and subsequently removing the protective groups, which process comprises carrying out the condensation in an anhydrous or water-containing aliphatic $C_2$–$C_4$ alcohol, in the presence of an acid acceptor.

2,4,6-Tris(aminophenylamino)triazines are important intermediates in dyestuff chemistry and are used, inter alia, for synthesizing textile, leather and paper dyes as well as pigments.

9 Claims, No Drawings

PROCESS FOR THE PREPARATION OF 2,4,6-TRIS(AMINOPHENYLAMINO)TRIAZINES

The present invention relates to a process for the preparation of 2,4,6-tris(aminophenylamino)triazines by condensing s-trichlorotriazine with three equivalents of partially protected phenylenediamine and subsequently removing the protective groups.

2,4,6-Tris(aminophenylamino)triazines are important intermediates for synthesising textile, leather and paper dyes as well as pigments. Up to three chromophoric radicals can be attached to the triazine nucleus through the diaminophenylene bridges, affording valuable substantive dyes that are particularly suitable for dyeing cotton and paper (q.v. German Offenlegungsschrift 32 23 436).

2,4,6-Trihalotriazines exhibit similar reactivity to acid halides (q.v. Houben-Weyl, Methoden der organischen Chemie, Vol. 5/4 (1960), p. 712). To avoid secondary reactions, therefore, nucleophilic substitutions at the halogenated triazine nucleus are ordinarily carried out in anhydrous aprotic solvents such as toluene, halobenzene or nitrobenzene (q.v. for example German Offenlegungsschrift 20 11 043). The drawback of this process is that the reaction product is in general readily soluble in these solvents and is therefore difficult to work up. The aim has therefore been to develop a process in which the protected tris(aminophenylamino)-triazine is present in solid form in the reaction medium at the conclusion of the reaction and can be isolated therefrom by means of simple filtration.

Hence it is the object of the present invention to provide a novel process by means of which the product obtained by reacting s-trichlorotriazine with 3 equivalents of a protected phenylenediamine is present in suspension in the reaction medium.

It has been found that the requirement of a suitable reaction medium is met by using aliphatic $C_2$–$C_4$ alcohols as solvents. 2,4,6-Tris(aminophenylamino)triazines are virtually insoluble in such alcohols and can be isolated in simple manner by known methods at the conclusion of the reaction. Removal of the protective groups then follows. Almost no reaction of the alcohol with the trichlorotriazine is observed. Even the disubstituted triazine is only sparingly soluble in the $C_2$–$C_4$ alcohols and is therefore able to precipitate. Surprisingly, however, this fact does not adversely affect the yield of desired trisubstituted product, the protected tris(aminophenylamino)triazine.

Accordingly, the present invention relates to a process for the preparation of 2,4,6-tris(aminophenylamino)triazines by condensing s-trichlorotriazine with 3 equivalents of a partially protected phenylenediamine and subsequently removing the protective groups, which process comprises carrying out the condensation in an anhydrous or water-containing aliphatic $C_2$–$C_4$ alcohol, in the presence of an acid acceptor.

Throughout this specification, 2,4,6-tris(aminophenylamino)triazines will be understood as meaning compounds of the following structure:

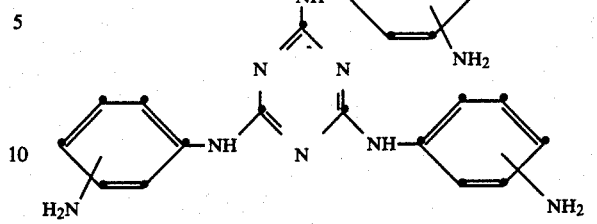

wherein the aromatic nucleus of the individual diaminophenylene radicals may additionally contain one or more substituents selected from halogen, e.g. fluorine, chlorine, bromine or iodine; cyano; and, in particular, $C_1$–$C_4$ alkyl such as methyl, ethyl, propyl, isopropyl or butyl, or $C_1$–$C_4$ alkoxy such as ethoxy, methoxy, propoxy, isopropoxy or butoxy. The amino group is located meta, or preferably para, to the respective amino bridge (—NH—).

The s-trichlorotriazine is reacted with a partially protected phenylenediamine, i.e. with an unsubstituted or substituted m- or p-phenylenediamine in which the amino group is blocked by a protective group. During the condensation, the hydrochloric acid formed is neutralised by an acid acceptor, so that the reaction mixture has a pH in the range of 7, i.e. suitable protective groups are those which are removable under acid as well as basic conditions. Reference is made in this connection to J. F. W. McOmie, Protective Groups in Organic Chemistry, Plenum Press 1973. It is preferred to use monoacylated phenylenediamines in the process of this invention. Particularly preferred protective groups are the acyl radicals of lower aliphatic carboxylic acids or aromatic carboxylic acids, e.g. the formyl, acetyl or benzoyl radical. The acetyl group is most preferably used to block one of the amino groups of the phenylenediamine.

As already mentioned, the partially protected phenylenediamine is employed in at least the 3-fold molar amount, based on s-trichlorotriazine. To achieve a substantially complete conversion, it is advantageous to use an excess of 10 to 15% by weight of partially protected phenylenediamine, based on the 3-fold molar amount.

It is preferred to use 4-aminoacetanilide as partially protected phenylenediamine.

In addition to ethanol, propanol and butanol, further suitable aliphatic $C_2$–$C_4$ alcohols are the corresponding secondary and tertiary alcohols, e.g. isopropanol, isobutanol and tert-butanol. The preferred reaction medium is ethanol. Good yields are also obtained by using isopropanol and n-butanol as solvent.

The presence of water in the alcohol has a favourable influence on the yield. Alcohols containing 1 to 10% by weight, preferably 3 to 7% by weight, of water are preferably used, i.e. those corresponding to commercially available technical alcohols. It is, of course, also possible to start from pure $C_2$–$C_4$ alcohols or from alcohols having a lower water content and, by adding water, to adjust them to the water content necessary for achieving an optimum yield. When using alcohols having a water content in excess of 10% by weight, is is only possible to achieve limited conversion of the disubstituted triazine, viz. the protected di(aminophenylamino)chlorotriazine, to the desired tris(aminophenylamino)triazine. Reaction in an absolute alcohol is possible, but the yield is usually about 10% lower than when using an alcohol with a lower water content. It may further be mentioned at this juncture that the reaction can also be carried out in dimethylformamide or sulfolane.

The acid acceptor employed in the process of the invention is e.g. an alkali metal carbonate or alkaline earth metal carbonate, a metal oxide or an alkali metal salt of an organic acid, e.g. an alkali metal acetate or an alkali metal alcoholate such as sodium ethylate. An aromatic amine may also be suitably employed, for example pyridine. The preferred acid acceptor is sodium ethylate, or anhydrous sodium carbonate which preferably has a particle size greater than 100 μm.

The acid acceptor is employed in an amount sufficient to neutralise the 3 moles of hydrochloric acid generated per mole of s-trichlorotriazine. An excess of 10 to 20% by weight is conveniently used.

After bringing together the partially protected phenylenediamine and s-trichlorotriazine, the reaction mixture exotherms initially to 40°-60° C. and, depending on the boiling point of the alcohol, is then advantageously heated to a temperature in the range from 60° to 130° C. It is best to heat the reaction mixture under reflux until complete conversion has been achieved. When using ethanol as solvent, the reaction is preferably carried out in the temperature range from 40° to 80° C. The reaction time is usually from 10 to 20 hours. The reaction course can be easily followed by e.g. thin-layer chromatography.

The process is conveniently carried out by charging the reactor with the partially protected phenylenediamine together with the acid acceptor in the alcohol and then adding the whole amount of s-trichlorotriazine all at once. Before adding the trichlorotriazine, it is expedient to stir the protected diamine and the acid acceptor to a homogeneous suspension. To prevent as far as possible the formation of hydrolysis or oxidation products, it is possible to carry out the reaction in an inert gas atmosphere, e.g. in a nitrogen atmosphere. The addition of the individual reactants can, of course, also be made in reverse order. Thus, for example, the reactor can be charged with the s-trichlorotriazine together with the acid acceptor in the alcohol and then the partially protected phenylenediamine is added.

Upon conclusion of the reaction, the tris)aminophenylamino)triazine which is protected at the amino groups is isolated from the reaction mixture by known methods, e.g. by filtration, centrifugation or decantation, and washed with alcohol and water. The still moist product — drying is not necessary — is then normally subjected to an acid hydrolysis to remove the protective groups. This is done by heating the product in e.g. dilute sulfuric acid for about 10 hours to a temperature of about 90°-110° C. The sulfuric acid desirably has a concentration of 5 to 40% by weight. After complete removal of the protective groups, the 2,4,6-tris(aminophenylamino)triazine is isolated by filtration and treated with e.g. an aqueous alkali metal hydroxide to effect complete removal of the sulfuric acid. Finally, the product is washed free of salts and dried.

The invention is illustrated by the following Examples in which parts and percentages are by weight. The NMR spectroscopic analysis is made using $d_6$-dimethyl sulfoxide as solvent. The δ-values are expressed in ppm relative to trimethylsilane and inner standard.

EXAMPLE 1

A heatable reactor equipped with reflux condenser is charged with 510 parts of 94% ethanol, 100 parts of 4-aminoacetanilide and 37 parts of anhydrous large-grained sodium carbonate (granular size 100–200 μm) and the mixture is stirred to a homogeneous suspension. To this suspension, which has a temperature of 20° C., are added 39 parts of s-trichlorotriazine all at once, with stirring. The condensation reaction commences immediately and the reaction mixture exotherms to 40°-55° C. The reaction mixture is then heated further to 60°-70° C. and stirred for 14 hours at this temperature. The reactor contents are then cooled to room temperature and the condensation product is isolated by filtration. The filter cake is washed with ethanol and water, affording 211 parts of a moist product containing 105 parts of 2,4,6-tris-(4'-acetyl-aminophenylamino)triazine. The NMR spectrum has signals with the following chemical displacements: δ=2.08 (singlet), acetyl-CH$_3$; δ=7.65 (pseudo-quartet), phenylene protons; δ=9.12 (singlet) and δ=9.85 (singlet), NH protons — intensity ratio 3:4:1:1.

To remove the acetyl groups, the moist product (211 parts) is added to a mixture of 940 parts of ice and 400 parts of 98% sulfuric acid. The mixture is then heated to 100° C. After 12 hours the acetyl groups are completely removed and the reaction mixture is allowed to cool to room temperature and the product is isolated by filtration. The crude product is washed with water and then, to remove by-products and any acid residue, suspended in 1900 parts of water and 140 parts of 30% sodium hydroxide solution and the suspension is refluxed. The product is isolated by filtration at 80° C. and the filter cake is washed with hot water and dried, affording 70 parts of 2,4,6-tris(aminophenylamino)triazine. The yield is 81%, based on s-trichlorotriazine.

EXAMPLE 2

100 parts of 4-aminoacetanilide and 47 parts of sodium ethylate are stirred to a homogeneous suspension in 510 parts of 94% ethanol and then 39 parts of s-trichlorotriazine are added at 20° C. The condensation commences immediately and the temperature rises to 40°-45° C. The reaction mixture is heated for 16 hours at reflux temperature to bring the reaction to completion. The reaction mixture is cooled to 20° C. and then filtered. The filter cake is washed with ethanol and water.

Removal of the protective groups is effected as described in Example 1. The final product consists of 1% of disubstituted and 82% of trisubstituted triazine, based on trichlorotriazine.

EXAMPLE 3

100 parts of 4-aminoacetanilide and 37 parts of sodium carbonate are stirred to a homogeneous suspension in 510 parts of isopropanol and then 39 parts of s-trichlorotriazine are added at 20° C. The condensation commences immediately and the temperature rises to 40°-45° C. The reaction mixture is heated for 20 hours at reflux temperature to bring the reaction to completion. The reaction mixture is cooled to 20° C. and then filtered. The filter cake is washed with isopropanol and water.

Removal of the protective groups is effected as described in Example 1. The final product consists of 0% of disubstituted and 85% of trisubstituted triazine, based on trichlorotriazine.

EXAMPLE 4

100 parts of 4-aminoacetanilide and 37 parts of sodium carbonate are stirred to a homogeneous suspension in 640 parts of sulfolane and then 39 parts of s-trichlorotriazine are added at 20° C. The condensation commences immediately and the temperature rises to 40°–45° C. The reaction mixture is heated for 3 hours at 75°–80° C. to bring the reaction to completion. The reaction mixture is cooled to 20° C. and then diluted with 5000 parts of water and the precipitated product is filtered and washed.

Removal of the protective groups is effected as described in Example 1. The final product consists of 1% of disubstituted and 86% of trisubstituted triazine, based on trichlorotriazine.

EXAMPLE 5

100 parts of 4-aminoacetanilide and 37 parts of sodium carbonate are stirred to a homogeneous suspension in 510 parts of dimethylformamide and then 39 parts of s-trichlorotriazine are added at 20° C. The condensation commences immediately and the temperature rises to 40°–45° C. The reaction mixture must be heated for 3 hours at 75° C. to bring the reaction to completion. To isolate the product, it is necessary to distill off 85% of the solvent and to precipitate the product with water.

Removal of the protective groups is effected as described in Example 1 after the product has been isolated by filtration and washed with water. The final product consists of 0% of disubstituted and 98% of trisubstituted triazine, based on trichlorotriazine.

EXAMPLE 6

100 parts of 4-aminoacetanilide and 37 parts of sodium carbonate are stirred to a homogeneous suspension in 510 parts of n-butanol and then 39 parts of s-trichlorotriazine are added at 20° C. The condensation commences immediately and the temperature rises to 40°–45° C. The reaction mixture is heated for 18 hours at 75°–80° C. and for 5 hours at 110° C. to bring the reaction to completion. The reaction mixture is cooled to 20° C. and the precipitated product is isolated by filtration and washed with n-butanol.

Removal of the protective groups is effected as described in Example 1. The final product consists of 1% of disubstituted and 66% of trisubstituted triazine, based on trichlorotriazine.

EXAMPLE 7

100 parts of 4-aminoacetanilide and 58 parts of sodium carbonate are stirred to a homogeneous suspension in 510 parts of absolute ethanol and the 39 parts of s-trichlorotriazine are added at 20° C. The condensation commences immediately and the temperature rises to 40°–45° C. The reaction mixture is heated for 18 hours at reflux temperature to bring the reaction to completion. The reaction mixture is cooled to 20° C. and then filtered. The filter cake is washed with ethanol and water.

Removal of the protective groups is effected as described in Example 1. The final product consists of 0% of disubstituted and 72% of trisubstituted triazine, based on trichlorotriazine.

EXAMPLE 8

100 parts of 4-aminoacetanilide and 58 parts of sodium carbonate are stirred to a homogeneous suspension in 510 parts of 91% ethanol and then 39 parts of s-trichlorotriazine are added at 20° C. The condensation commences immediately and the temperature rises to 40°–45° C. The reaction mixture is heated for 18 hours at reflux temperature to bring the reaction to completion. The reaction mixture is cooled to 20° C. and then filtered. The filter cake is washed with ethanol and water.

Removal of the protective groups is effected as described in Example 1. The final product consists of 0% of disubstituted and 68% of trisubstituted triazine, based on trichlorotriazine.

What is claimed is:

1. A process for the preparation of 2,4,6-tris(aminophenylamino)triazines by condensing s-trichlorotriazine with 3 equivalents of a partially protected phenylenediamine and subsequently removing the protective groups, which process comprises carrying out the condensation in an anhydrous or water-containing aliphatic $C_2$–$C_4$ alcohol, in the presence of an acid acceptor.

2. A process according to claim 1, wherein the alcohol is ethanol, isopropanol or n-butanol.

3. A process according to claim 2, wherein the alcohol is ethanol.

4. A process according to claim 1, wherein the alcohol contains 1 to 10% by weight of water.

5. A process according to claim 4, wherein the alcohol contains 3 to 7% by weight of water.

6. A process according to claim 1, wherein the acid acceptor is an alkali metal carbonate or an alkaline earth metal carbonate, an alkali metal salt of an organic acid, an alkali metal alcoholate or pyridine.

7. A process according to claim 6, wherein the acid acceptor is sodium ethylate or anhydrous sodium carbonate which preferably has a granular size larger than 100 μm.

8. A process according to claim 1, wherein the reaction is carried out in the temperature range from 40° to 130° C.

9. A process according to claim 1, wherein the partially protected phenylenediamine is 4-aminoacetanilide.

* * * * *